United States Patent [19]

Hanko et al.

[11] Patent Number: 5,318,980

[45] Date of Patent: Jun. 7, 1994

[54] SULPHONYLBENZYL-SUBSTITUTED IMIDAZOLES

[75] Inventors: Rudolf Hanko, Duesseldorf; Jürgen Dressel, Wuppertal; Peter Fey, Wuppertal; Walter Hübsch, Wuppertal; Thomas Krämer, Wuppertal; Ulrich E. Müller, Wuppertal; Matthias Müller-Gliemann, Solingen-Ohligs; Martin Beuck, Erkrath; Stanislav Kazda; Claudia Hirth-Dietrich, both of Wuppertal; Andreas Knorr, Erkrath; Johannes-Peter Stasch, Wuppertal; Stefan Wohlfeil, Hilden; Özkan Yalkinoglu, Wuppertal, all of Fed. Rep. of Germany

[73] Assignee: Bayer Aktiengesellschaft, Leverkusen, Fed. Rep. of Germany

[21] Appl. No.: 18,961

[22] Filed: Feb. 18, 1993

[30] Foreign Application Priority Data

Feb. 27, 1992 [DE] Fed. Rep. of Germany ....... 4206043

[51] Int. Cl.$^5$ ................. A61K 31/535; A61K 31/495; A61K 31/415; C07D 413/12
[52] U.S. Cl. ..................... 514/326; 514/79; 514/85; 514/89; 514/91; 514/94; 514/255; 514/235.8; 514/381; 514/397; 544/139; 544/337; 544/370; 546/210; 548/111; 548/112; 548/252; 548/253; 548/314.7

[58] Field of Search ............ 514/79, 85, 89, 91, 514/94, 255, 235.8, 326, 381, 397; 544/139, 337, 370; 546/210; 548/252, 253, 314.7, 111, 112

[56] References Cited

U.S. PATENT DOCUMENTS 5,138,069 8/1992 Carini et al. ................. 548/253
5,185,351 2/1993 Finkelstein et al. ............ 514/341

FOREIGN PATENT DOCUMENTS 0324377 7/1989 European Pat. Off. .
0403158 12/1990 European Pat. Off. .
0403159 12/1990 European Pat. Off. .

OTHER PUBLICATIONS

J. C. Sheehan, S. L. Ledis, J. Am. Chem. Soc. 95, 875 (1973).
F. E. Frerman et al., J. Biol. Chem. 258, 7087-7093 (1983).
N. B. Benoiton, K. Klurada, Int. Pept. Prot. Res. 17, 197 (1981).
R. Ross, J. Cell. Biol. 50, 172, 1971.

*Primary Examiner*—Patricia L. Morris
*Attorney, Agent, or Firm*—Sprung Horn Kramer & Woods

[57] ABSTRACT

Sulphonylbenzyl-substituted imidazoles can be prepared by first reacting imidazolylaldehydes with sulphonylbenzyl compounds and then oxidising or reducing the aldehyde function in the customary manner.

The sulphonylbenzyl-substituted imidazoles can be used as active compounds in medicaments.

10 Claims, No Drawings

SULPHONYLBENZYL-SUBSTITUTED IMIDAZOLES

The invention relates to sulphonylbenzyl-substituted imidazoles, a process for their preparation and their use in medicaments, in particular as antihypotensive and antiatherosclerotic agents.

It is known that renin, a proteolytic enzyme, splits off the decapeptide angiotensin I from angiotensinogen in vivo, and the angiotensin I in turn is degraded in the lung, the kidneys or other tissues to give the hypertensive octapeptide angtiotensin II. The various effects of angiotensin II, such as vasoconstriction, Na+ retention in the kidney, release of aldosterone in the adrenals and an increase in the tonicity of the sympathetic nervous system, have a synergistic effect in the sense of increasing the blood pressure.

Angiotensin II moreover has the property of promoting the growth and multiplication of cells such as cardiac muscle cells and smooth muscle cells, these growing and proliferating to an increased extent during various disease states (for example hypertension, atherosclerosis and cardiac insufficiency).

A possible use for intervention in the renin-angiotensin system (RAS) is, in addition to inhibition of renin activity, inhibition of the activity of angiotensin-converting enzyme (ACE) and blockade of angiotensin II receptors. Phenyl(alkyl)imidazole acids and imidazolylalkene acids are described in the publications EP 324 377 A2, EP 403 158 A2 and EP 403 159 A2.

The present invention relates to compounds of the general formula (I)

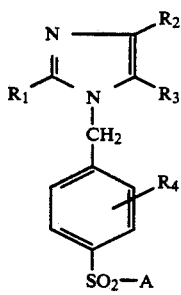

in which $R^1$ represents straight-chain or branched alkyl or alkenyl having in each case up to 8 carbon atoms, which are optionally substituted by cycloalkyl having 3 to 6 carbon atoms, or represents cycloalkyl having 3 to 8 carbon atoms, $R^2$ represents hydrogen or halogen, or represents straight-chain or branched perfluoroalkyl having up to 8 carbon atoms, $R^3$ represents straight-chain or branched alkyl having up to 6 carbon atoms, which is substituted by hydroxyl or straight-chain or branched alkoxy having up to 4 carbon atoms, or represents a group of the formula —CO—$R^5$ or —CO—NR$^6$R$^7$,
wherein $R^5$ denotes hydrogen, straight-chain or branched alkoxy having up to 8 carbon atoms, hydroxyl, benzyloxy or phenoxy, $R^6$ and $R^7$ are identical or different and denote hydrogen, straight-chain or branched alkyl having up to 8 carbon atoms or phenyl, $R^4$ represents hydrogen, halogen or straight-chain or branched alkyl having up to 8 carbon atoms, or represents straight-chain or branched perfluoroalkyl having up to 6 carbon atoms, or represents a group of the formula —OX,
wherein X denotes hydrogen, benzyl, a hydroxyl protective group or denotes straight-chain or branched alkyl having up to 8 carbon atoms, A represents a 3- to 8-membered saturated heterocyclic radical which is bonded via the nitrogen atom, contains up to 2 further hetero atoms from the series comprising S, N and O and is optionally substituted up to twice in an identical or different manner by perfluoroalkyl having up to 5 carbon atoms or by a radical of the formula

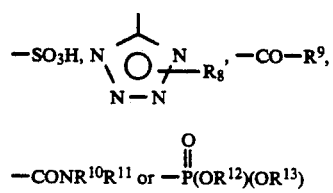

$$-CONR^{10}R^{11} \text{ or } -\overset{O}{\underset{\|}{P}}(OR^{12})(OR^{13})$$

wherein $R^8$ denotes hydrogen, straight-chain or branched alkyl having up to 6 carbon atoms or triphenylmethyl, $R^9$ has the abovementioned meaning of $R^5$ and is identical to or different from this radical, $R^{10}$ and $R^{11}$ have the abovementioned meaning of $R^6$ and $R^7$ and are identical to or different from these radicals and $R^{12}$ and $R^{13}$ are identical or different and denote hydrogen, straight-chain or branched alkyl having up to 8 carbon atoms or phenyl, and salts thereof.

The sulphonylbenzyl-substituted imidazoles according to the invention can also be present in the form of their salts. Salts with organic or inorganic bases or acids may be mentioned in general here.

Physiologically acceptable salts are preferred in the context of the present invention. Physiologically acceptable salts of the sulphonylbenzyl-substituted imidazoles can be salts of the substances according to the invention with mineral acids, carboxylic acids or sulphonic acids. Particularly preferred salts are, for example, those with hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, citric acid, fumaric acid, maleic acid or benzoic acid.

Physiologically acceptable salts can also be metal salts or ammonium salts of the compounds according to the invention which have a free carboxyl group. Salts which are particularly preferred are, for example, the sodium, potassium, magnesium or calcium salts, and ammonium salts which are derived from ammonia or organic amines such as ethylamine, di- or triethylamine, di- or triethanolamine, dicyclohexylamine, dimethylaminoethanol, arginine, lysine or ethylenediamine.

The compounds according to the invention can exist in stereoisomeric forms, either as enantiomers or as diastereomers. The invention relates both to the enantiomers or diastereomers and to their particular mixtures. The racemic forms can be separated into the stereoisomerically uniform constituents in a known manner, like the diastereomers (compare E. L. Eliel, Stereochemistry of Carbon Compounds, McGraw Hill, 1962).

A 3- to 8-membered saturated heterocyclic radical which is bonded via N and moreover can contain up to 2 oxygen, sulphur and/or nitrogen atoms as hetero atoms in general represents azetidinyl, piperidyl, morpholinyl, piperazinyl or pyrrolidinyl. 5- and 6-membered rings having one oxygen and/or up to 2 nitrogen atoms, such as piperidyl, morpholinyl or pyrrolidinyl, are preferred. Piperidyl and pyrrolidinyl are particularly preferred.

Preferred compounds of the general formula (I) are those in which $R^1$ represents straight-chain or branched alkyl or alkenyl having in each case up to 6 carbon atoms, which are optionally substituted by cyclopropyl, cyclobutyl, cyclopentyl or cyclohexyl, or represents cyclopropyl, cyclobutyl, cyclopentyl or cyclohexyl, $R^2$ represents hydrogen, fluorine, chlorine or bromine, or represents straight-chain or branched perfluoroalkyl having up to 6 carbon atoms, $R^3$ represents straight-chain or branched alkyl having up to 4 carbon atoms, which is substituted by hydroxyl, methoxy or ethoxy, or represents a group of the formula —CO—$R^5$ or —CO—$NR^6R^7$, wherein $R^5$ denotes hydrogen, straight-chain or branched alxoxy having up to 6 carbon atoms, hydroxyl, benzyloxy or phenoxy, $R^6$ and $R^7$ are identical or different and denote hydrogen or straight-chain or branched alkyl having up to 6 carbon atoms, $R^4$ represents hydrogen, fluorine, chlorine, bromine or straight-chain or branched alkyl having up to 6 carbon atoms, or represents straight-chain or branched perfluoroalkyl having up to 4 carbon atoms, or represents a group of the formula —OX, wherein X denotes hydrogen, benzyl, acetyl, or denotes straight-chain or branched alkyl having up to 6 carbon atoms, A represents azetidinyl, piperidyl, pyrrolidinyl or morpholinyl which are bonded via the nitrogen atom and are optionally substituted by trifluoromethyl or by a radical of the formula

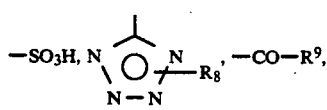

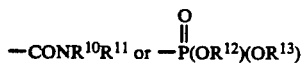

wherein $R^8$ denotes hydrogen, straight-chain or branched alkyl having up to 4 carbon atoms or triphenylmethyl, $R^9$ has the abovementioned meaning of $R^5$ and is identical to or different from this radical, $R^{10}$ and $R^{11}$ have the abovementioned meaning of $R^6$ and $R^7$ and are identical to or different from these radicals and $R^{12}$ and $R^{13}$ are identical or different and denote hydrogen, straight-chain or branched alkyl having up to 6 carbon atoms or phenyl, and salts thereof.

Particularly preferred compounds of the general formula (I) are those in which $R^1$ represents straight-chain or branched alkyl or alkenyl having in each case up to 4 carbon atoms or cyclopropyl, $R^2$ represents hydrogen, fluorine or chlorine, or represents straight-chain or branched perfluoroalkyl having up to 4 carbon atoms, $R^3$ represents the —$CH_2OH$ group, or represents a group of the formula —CO—$R^5$ or —CO—$NR^6R^7$, wherein $R^5$ denotes hydrogen, straight-chain or branched alkoxy having up to 4 carbon atoms, hydroxyl, benzyloxy or phenoxy, $R^6$ and $R^7$ are identical or different and denote hydrogen or straight-chain or branched alkyl having up to 4 carbon atoms, $R^4$ represents hydrogen, fluorine, chlorine or straight-chain or branched alkyl having up to 4 carbon atoms, or represents straight-chain or branched perfluoroalkyl having up to 3 carbon atoms, or represents a group of the formula —OX, wherein X denotes hydrogen, benzyl, acetyl or denotes straight-chain or branched alkyl having up to 6 carbon atoms, A represents piperidyl or pyrrolidinyl which are bonded via the nitrogen atom and are optionally substituted by trifluoromethyl or by a radical of the formula

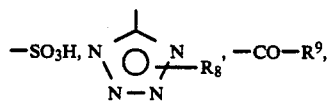

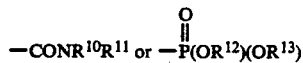

wherein $R^8$ denotes hydrogen, methyl, ethyl or triphenyl, $R^9$ has the abovementioned meaning of $R^5$ and is identical to or different from this radical, $R^{10}$ and $R^{11}$ have the abovementioned meaning of $R^6$ and $R^7$ and are identical to or different from these radicals and $R^{12}$ and $R^{13}$ are identical or different and denote hydrogen, straight-chain or branched alkyl having up to 4 carbon atoms or phenyl, and salts thereof.

A process has furthermore been found for the preparation of the compounds of the general formula (I) according to the invention, characterised in that aldehydes of the general formula (II)

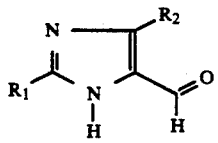

in which
R¹ and R² have the abovementioned meaning,
are first reacted with compounds of the general formula (III)

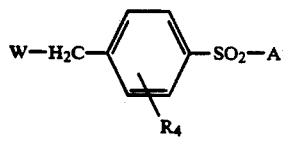

in which
R⁴ and A have the abovementioned meaning
and
W represents halogen, preferably bromine,
in inert solvents, if appropriate in the presence of a base, and the aldehyde function, if appropriate, is then oxidised or reduced by customary methods, in the case of esters the acids are also subsequently esterified by the customary method, and in the case of acids the esters are hydrolysed,
in the case of amides amidation follows, if appropriate via an activated carboxylic acid stage, in the presence of a base and/or a dehydrating substance, and in the case where R⁸≠H alkylation follows.

The process according to the invention can be illustrated by way of example by the following equation:

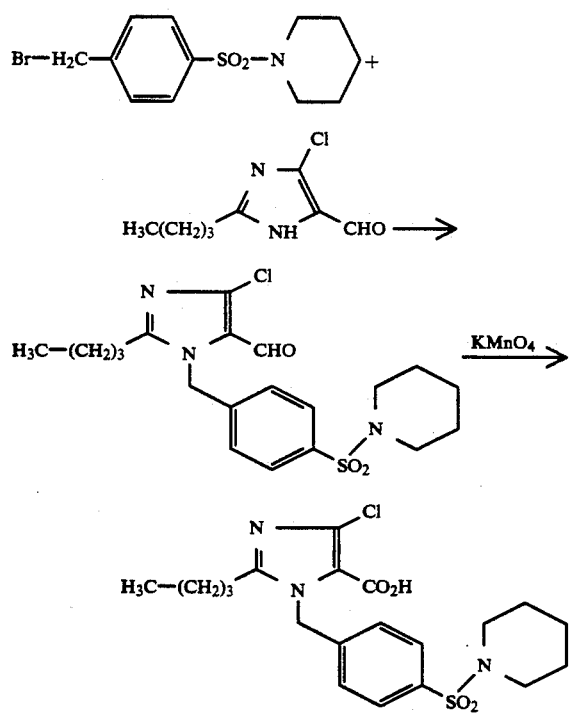

Suitable solvents for the individual steps of the process are the customary organic solvents which do not change under the reaction conditions. These include, preferably, ethers such as diethyl ether, dioxane, tetrahydrofuran and glycol dimethyl ether, or hydrocarbons such as benzene, toluene, xylene, hexane, cyclohexane, or petroleum fractions, or halogenohydrocarbons such as methylene chloride, chloroform, carbon tetrachloride, dichloroethylene, trichloroethylene or chlorobenzene, or ethyl acetate, or alcohols such as methanol, ethanol and tert-butanol, or triethylamine, pyridine, dimethyl sulphoxide, dimethylformamide, hexamethylphosphoric acid triamide, acetonitrile, acetone or nitromethane. It is likewise possible to use mixtures of the solvents mentioned. Tetrahydrofuran, methylene chloride, toluene and dimethylformamide are preferred for the various steps.

Inorganic or organic bases can in general be employed as bases. These include, preferably, alkali metal hydroxides such as sodium hydroxide or potassium hydroxide, alkaline earth metal hydroxides such as barium hydroxide, alkali metal carbonates such as sodium carbonate or potassium carbonate, alkaline earth metal carbonates such as calcium carbonate, or alkali metal or alkaline earth metal alcoholates or amides, such as sodium or potassium methanolate, sodium or potassium ethanolate or potassium tert-butylate or lithium diisopropylamide (LDA), or organic amines (trialkyl($C_1$-$C_6$-)amines) such as triethylamine or N,N-diisopropylamine, or heterocyclic compounds such as 1,4-diazabicyclo[2.2.2]octane (DABCO), 1,8-diazabicyclo(5.4.0)undec-7-ene (DBU), pyridine, diaminopyridine, methylpiperidine or morpholine. It is also possible to use alkali metals, such as sodium, or hydrides thereof, such as sodium hydride, as the bases. Sodium hydride is preferred.

The base is in general employed in an amount of 0.05 mol to 10 mol, preferably 1 mol to 2 mol, per mole of the compound of the formula (III).

The process according to the invention is in general carried out in a temperature range from −20° C. to +100° C., preferably from 0° C. to +80° C. The process according to the invention is in general carried out under normal pressure. However, it is also possible to carry out the process under increased pressure or under reduced pressure (for example in a range from 0.5 to 5 bar).

The oxidation is in general carried out in one of the abovementioned solvents, preferably with tert-butanol, using oxidising agents such as potassium permanganate, chromyl chloride, cerium ammonium nitrate, silver oxide, selenium dioxide or a chromium (VI) oxide in combination with acetic anhydride. Potassium permanganate is preferred.

The oxidation can be carried out under normal pressure or under increased or reduced pressure (for example from 0.5 to 5 bar), preferably under normal pressure. It is carried out in a temperature range from 0° C. to +40° C., preferably at room temperature.

The reduction of alkoxycarbonyl compounds or aldehydes to give the corresponding alcohols is in general carried out with hydrides such as lithium aluminium hydride or sodium borohydride, preferably with sodium borohydride, in inert solvents such as ethers, hydrocarbons or alcohols or mixtures thereof, preferably in ethers such as diethyl ether, tetrahydrofuran or dioxane, or alcohols such as ethanol, and in the case of the aldehydes preferably with sodium borohydride in tetrahydrofuran, in a temperature range from 0° C. to +150°

C., preferably from +20° C. to +80° C., under normal pressure.

Suitable solvents for the alkylation are customary organic solvents which do not change under the reaction conditions. These include, preferably, ethers such as diethyl ether, dioxane, tetrahydrofuran and glycol dimethyl ether, or hydrocarbons such as benzene, toluene, xylene, hexane and cyclohexane, or petroleum fractions, or halogenohydrocarbons such as methylene chloride, chloroform, carbon tetrachloride, dichloroethylene, trichloroethylene and chlorobenzene, or ethyl acetate, or triethylamine, pyridine, dimethyl sulphoxide, dimethylformamide, hexamethylphosphoric acid triamide, acetonitrile, acetone or nitromethane. It is also possible to use mixtures of the solvents mentioned. Methylene chloride is preferred.

The alkylation is carried out in the abovementioned solvents at temperatures from 0° C. to +150° C., preferably at room temperatures up to +100° C., under normal pressure.

The amidation is in general carried out in inert solvents in the presence of a base and a dehydrating agent.

Suitable solvents here are inert organic solvents which do not change under the reaction conditions. These include halogenohydrocarbons such as methylene chloride, chloroform, carbon tetrachloride, 1,2-dichloroethane, trichloroethane, tetrachloroethane, 1,2-dichloroethane and trichloroethylene, hydrocarbons such as benzene, xylene, toluene, hexane and cyclohexane, or petroleum fractions, nitromethane, dimethylformamide, acetonitrile or hexamethylphosphoric acid triamide. It is also possible to employ mixtures of the solvents. Methylene chloride is particularly preferred.

Suitable bases for the amidation are the customary basic compounds. These include, preferably, alkali metal and alkaline earth metal hydroxides such as lithium hydroxide, sodium hydroxide, potassium hydroxide and barium hydroxide, alkali metal hydrides such as sodium hydride, alkali metal or alkaline earth metal carbonates such as sodium carbonate and potassium carbonate, or alkali metal alcoholates such as sodium methanolate or ethanolate, potassium methanolate or ethanolate and potassium tert-butylate, or organic amines such as benzyltrimethylammonium hydroxide, tetrabutylammonium hydroxide, pyridine, triethylamine and N-methylpiperidine.

The amidation is carried out in a temperature range from 0° C. to 150° C., preferably at 25° C. to 40° C.

The amidation is in general carried out under normal pressure. However, it is also possible to carry out the process under reduced pressure or under increased pressure (for example in a range from 0.5 to 5 bar).

In carrying out the amidation, the base is in general employed in an amount of 1 to 3 mol, preferably 1 to 1.5 mol, per mole of the corresponding carboxylic acid.

Suitable dehydrating reagents are carbodiimides such as diisopropylcarbodiimide, dicyclohexylcarbodiimide and N-(3-dimethylaminopropyl)-N'-ethylcarbodiimide hydrochloride, or carbonyl compounds such as carbonyldiimidazole, or 1,2-oxazolium compounds such as 2-ethyl-5-phenyl-1,2-oxazolium 3-sulphonate, or propanephosphoric anhydride or isobutyl chloroformate or benzotriazolyloxy-tris-(dimethylamino)phosphonium hexafluorophosphate or phosphonic acid diphenyl ester-amide or methanesulphonyl chloride or thionyl chloride, if appropriate in the presence of bases such as triethylamine or N-ethylmorpholine or N-methylpiperidine or dicyclohexylcarbodiimide and N-hydroxysuccinimide (compare J. C. Sheehan, S. L. Ledis, J. Am. Chem. Soc. 95, 875 (1973); F. E. Freeman et al., J. Biol. Chem. 225, 507 (1982) and N. B. Benoton, K. Kluroda, Int. Pept. Prot. Res. 13, 403 (1979), 17, 187 (1981)).

The esterification is carried out by customary methods by reacting the corresponding carboxylic acid ($R^5$—OH), if appropriate also via an activated stage, with the corresponding alcohols in a temperature range from −20° C. to +120° C., preferably at 20° C., and under normal pressure.

The hydrolysis of the carboxylic acid esters is carried out by customary methods by treating the esters with customary bases in inert solvents. Suitable bases for the hydrolysis are the customary inorganic bases. These include, preferably, alkali metal hydroxides or alkaline earth metal hydroxides, such as sodium hydroxide, potassium hydroxide or barium hydroxide, or alkali metal carbonates such as sodium or potassium carbonate and sodium bicarbonate. Sodium hydroxide and potassium hydroxide are particularly preferably employed.

Suitable solvents for the hydrolysis are water or the organic solvents customary for hydrolysis. These include, preferably, alcohols such as methanol, ethanol, propanol, isopropanol and butanol, or ethers such as tetrahydrofuran and dioxane, or dimethylformamide or dimethyl sulphoxide. Alcohols such as methanol, ethanol, propanol and isopropanol, are particularly preferably used. It is also possible to employ mixtures of the solvents mentioned.

The hydrolysis is in general carried out in a temperature range from 0° C. to +100° C., preferably from +20° C. to +80° C.

The hydrolysis is in general carried out under normal pressure. However, it is also possible to carry out the hydrolysis under reduced pressure or under increased pressure (for example from 0.5 to 5 bar).

In carrying out the hydrolysis, the base is in general employed in an amount of 1 to 3 mol, preferably 1 to 1.5 mol, per mole of the ester. Molar amounts of the reactants are particularly preferably used.

The compounds of the general formula (III) are new and can be prepared by a process in which substituted benzylsulphonic acid chlorides of the general formula (IV)

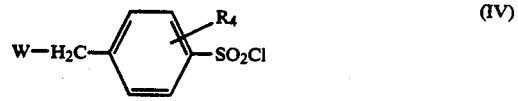

in which
$R^4$ and W have the abovementioned meaning,
are reacted with compounds of the general formula (V)

in which
A has the abovementioned meaning,
in one of the abovementioned solvents and bases, preferably in methylene chloride with triethylamine.

The reaction is in general carried out under normal pressure. However, it is also possible to carry out the reaction under reduced pressure or under increased pressure (for example from 0.5 to 5 bar).

In carrying out the reaction, the base is in general employed in an amount of 1 to 3 mol, preferably 1 to 1.5 mol, per mole of the compounds of the general formula (IV). Molar amounts of the reactants are particularly preferably used.

The reaction is in general carried out in a temperature range from −40° C. to +40° C., preferably from −30° C. to 0° C., and under normal pressure.

The compounds of the general formulae (IV) and (V) are known or can be prepared by the customary method.

The compounds of the general formula (II) are known or can be prepared by the customary method [compare, for example, Beilstein 9, 511].

The compounds of the general formula (I) according to the invention exhibit an unforeseeable, useful pharmacological action spectrum.

The compounds according to the invention have a specific A II antagonistic action, since they inhibit the bonding of angiotensin II to A II receptors. They suppress the vasoconstrictive and aldosterone secretion-stimulating effects of angiotensin II. They moreover inhibit the proliferation of smooth muscle cells.

They can therefore be employed in medicaments for the treatment of arterial hypertension and atherosclerosis. Moreover, they can be employed for the treatment of coronary heart diseases, cardiac insufficiency, disturbances in cerebral performance, ischaemic cerebral diseases, disturbances in peripheral blood circulation, functional disturbances of the kidney and adrenals, diseases of the respiratory passages of bronchospastic and vascular origin, sodium retention and oedemas. The substances moreover have a natriuretic and diuretic action. This action manifests itself in a mobilisation of oedema fluid in cases of pathological fluid increase of cardiac and non-cardiac origin.

Investigation of the Inhibition of Contraction Induced with Agonists

Rabbits of both sexes are stunned by a blow to the neck and exsanguinated or, where appropriate, anaesthetised with Nembutal (about 60–80 mg/kg i.v.) and sacrificed by opening the thorax. The thoracic aorta is removed, freed from attached connective tissue and divided into ring segments 1.5 mm wide, and the segments are introduced individually, under an initial load of about 3.5 g, into 10 ml organ baths containing carbogen-gassed KrebsHenseleit nutrient solution thermostatically controlled at 37° C. and having the following composition: 119 mmol/l of NaCl; 2.5 mmol/l of $CaCl_2 \times 2\ H_2O$; 1.2 mmol/l to $KH_2PO_4$; 10 mmol/l of glucose; 4.8 mmol/l of KCl; 1.4 mmol/l of $MgSO_4 \times 7\ H_2O$ and 25 mmol/l of $NaHCO_3$.

The contractions are recorded isometrically by Statham UC2 cells via a bridge amplifier (ifd Mülheim or DSM Aalen), and are digitalised and evaluated by means of an A/D converter (system 570, Keithley Munich). The agonist dose/effect curves (DEC) are plotted hourly. For each DEC, 3 or 4 individual concentrations are applied to the baths at intervals of 4 minutes. The DEC and subsequent wash-out cycles (16 times for about 5 sec/min each with the above nutrient solution) are followed by a 28-minute resting or incubation phase, within which the contractions as a rule reach the starting value again.

The level of the 3rd DEC in the normal case is used as a reference parameter for evaluating the test substance which is to be investigated in subsequent passes and, for the subsequent DECs, is applied to the baths at the start of the incubation time in a dosage which increases each time. Each aortic ring is stimulated with always the same agonist over the entire day.

| Agonists and their standard concentrations (application volume per individual dose = 100 μl): | | |
|---|---|---|
| KCl | 22.7;32.7;42.7;52.7 | mmol/l |
| l-noradrenaline | $3 \times 10^{-9}; 3 \times 10^{-8}; 3 \times 10^{-7}; 3 \times 10^{-6}$ | g/ml |
| serotonin | $10^{-8}; 10^{-7}; 10^{-6}; 10^{-5}$ | g/ml |
| B-HT 920 | $10^{-7}; 10^{-6}; 10^{-5}$ | g/ml |
| methoxamine | $10^{-7}; 10^{-6}; 10^{-5}$ | g/ml |
| angiotensin II | $3 \times 10^{-9}; 10^{-8}; 3 \times 10^{-8}; 10^{-7}$ | g/ml |

The effect in each case at the 3rd=submaximum agonist concentration is taken as a basis for calculation of the $IC_{50}$ (concentration at which the substance to be investigated causes 50% inhibition).

The compounds according to the invention inhibit angiotensin II-induced contraction of the isolated rabbit aorta as a function of the dose. The contraction induced by potassium depolarisation or other agonists was not inhibited or was only slightly inhibited at high concentrations.

TABLE A

Inhibition of vascular contraction on isolated aortic rings of rabbits in vitro
$IC_{50}$ [nM] against contractions induced by:

| Example No.: | AII |
|---|---|
| 15 | 202 |
| 16 | 309 |
| 19 | 44 |
| 25 | 5 |
| 21 | 250 |

Blood Pressure Measurements on Angiotensin II-Infused Rats

Male Wistar rats (Moellegaard, Copenhagen, Denmark) having a body weight of 300–350 g are anaesthetised with thiopental (100 mg/kg i.p.). After tracheotomy, a catheter for blood pressure measurement is inserted into the femoral artery and a catheter for angiotensin II infusion and a catheter for administration of the substance are inserted into the femoral veins. After administration of the ganglion blocker pentolinium (5 mg/kg i.v.), the angiotensin II infusion (0.3 μg/kg/minute) is started. As soon as the blood pressure values have reached a stable plateau, the test substances are administered either intravenously, or orally as a suspension or solution in 0.5% tylose. The changes in blood pressure under the influence of the substance are stated as the mean values±SEM in the table.

Determination of the Antihypertensive Activity on Conscious Hypertensive Rats The oral antihypertensive activity of the compounds according to the invention was tested on conscious rats with surgically induced unilateral renal artery stenosis. For this purpose, the right renal artery was constricted with a silver clip of 0.18 mm internal diameter. With this form of hypertension, the plasma renin activity is increased in the first six weeks after the attack. The arterial blood pressure of these animals was measured bloodlessly with a "tall cuff" at defined intervals of time after administration of the substance. The substances to be tested were administered intragastrally ("orally") via a stomach tube in various doses as a suspension in a tylose suspension. The compounds according to the invention lower the arterial blood pressure of hypertensive rats in a clinically relevant dosage.

The compounds according to the invention moreover inhibit specific bonding of radioactive angiotensin II as a function of the concentration.

Interaction of the Compounds According to the Invention with the Angiotensin II Receptor on Membrane Fractions of the Adrenal Cortex (Cattle)

Adrenal cortices from cattle (AC), which are freshly removed and carefully freed from medulla from the capsule, are comminuted to a coarse membrane homogenate in sucrose solution (0.32M) with the aid of an Ultra-Turrax (Janke & Kunkel, Staufen i.B.), and the homogenate is partly purified to membrane fractions in two centrifugation steps.

The investigations on receptor bonding are carried out on partly purified membrane fractions of bovine AC with radioactive angiotensin II in an assay volume of 0.25 ml, which specifically contains the partly purified membranes (50–80 $\mu$g), $^3$H-angiotensin II (3–5 nM), test buffer solution (50 mM Tris, pH 7.2), 5 mM $MgCl_2$ and the substances to be investigated. After an incubation time of 60 minutes at room temperature, the non-bonded radioactivity of the samples is separated off by means of moistened glass fibre filters (Whatman GF/C), and, after the protein has been washed with ice-cold buffer solution (50 mM Tris/HCl, pH 7.4, 5% PEG 6000), the radioactivity bonded is measured spectrophotometrically in a scintillation cocktail. The raw data were analysed with computer programs to give $K_i$ and $IC_{50}$ values ($K_i$: $IC_{50}$ values corrected for the radioactivity used; $IC_{50}$ values: concentration at which the substance to be investigated causes 50% inhibition of specific bonding of the radioligand).

| Example No. 15 | $K_i$ = 400 nM |
| Example No. 18 | $K_i$ = 200 nM |

Investigation of the Inhibition of the Proliferation of Smooth Muscle Cells by the Compounds According to the Invention Smooth muscle cells which are obtained from the aortas of rats or pigs by the media explantate technique are used to determine the antiproliferative action of the compounds [R. Ross, J. Cell. Biol. 50, 172, 1971]. The cells are sown in suitable culture dishes, as a rule 24-hole plates, and cultured for 2–3 days in medium 199 containing 7.5% of FCS and 7.5% of NCS, 2 mM of L-glutamine and 15 mM of HEPES, pH 7.4, in 5% $CO_2$ at 37° C. Thereafter, the cells are synchronised by serum withdrawal for 2–3 days and then stimulated to growth with AII, serum or other factors. Test compounds are added at the same time. After 16–20 hours, 1 $\mu$Ci of $^3$H-thymidine is added, and after a further 4 hours, the incorporation of this substance into the TCA-precipitatable DNA of the cells is determined.

| Example No. | % inhibition at $10^6$M |
|---|---|
| 11 | 20 |
| 12 | 70 |

Test for Natriuretic Action

Fasting Wistar rats are treated orally with the test substance (suspended in tylose solution). The urine excreted over 6 hours is then collected in diuresis cages. The concentration of sodium and potassium in the urine is determined by flame photometry.

The new active compounds can be converted in a known manner into the customary formulations such as tablets, coated tablets, pills, granules, aerosols, syrups, emulsions, suspensions and solutions, using inert, non-toxic, pharmaceutically suitable excipients or solvents. The therapeutically active compound should in each case be present here in a concentration of about 0.5 to 90% by weight of the total mixture, that is to say in amounts which are sufficient to achieve the stated dosage range.

The formulations are prepared, for example, by extending the active compounds with solvents and/or excipients, if appropriate using emulsifying agents and/or dispersing agents, and, for example in the case where water is used as the diluent, organic solvents can be used as auxiliary solvents if appropriate.

The compounds are administered in the customary manner, preferably orally or parenterally, in particular perlingually or intravenously.

In the case of parenteral use, solutions of the active compound can be employed, using suitable liquid excipient materials.

In general, it has proved advantageous, in the case of intravenous administration, to administer amounts of about 0.001 to 1 mg/kg, preferably about 0.01 to 0.5 mg/kg of body weight to achieve effective results, and in the case of oral administration, the dosage is about 0.01 to 20 mg/kg, preferably 0.1 to 10 mg/kg of body weight.

Nevertheless, it may at times be necessary to deviate from the amounts mentioned, and in particular to do so as a function of the body weight or of the nature of the administration route, of the behaviour of the individual towards the medicament, of the nature of its formulation and of the time or interval at which administration takes place. Thus, in some cases it may be sufficient to manage with less than the abovementioned minimum amount, while in other cases the upper limit mentioned must be exceeded. Where relatively large amounts are administered, it may be advisable to divide these into several individual doses over the course of the day.

| Mobile phase mixtures: | |
|---|---|
| a = petroleum ether/ethyl acetate | 1:1 |
| b = $CH_2Cl_2$/ethyl acetate | 5:1 |
| c = $CH_2Cl_2$/$CH_3OH$ | 3:1 |
| d = $CH_2Cl_2$/ $CH_3OH$ | 10:1 |

STARTING COMPOUNDS

EXAMPLE I 4-(Bromomethyl)benzenesulphonyl chloride

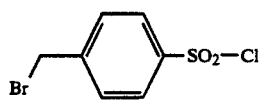

38.1 g (0.2 mol) of 4-methylbenzenesulphonyl chloride are dissolved in 300 ml of carbon tetrachloride, 35.6 g (0.2 mol) of N-bromosuccinimide are added and, after addition of 0.2 g (1.2 mmol) of azobisisobutyronitrile (ABU), the mixture is heated under reflux for 4 hours. After cooling, the solids are filtered off and the filtrate is freed from the solvent. Flash chromatography (petroleum ether/toluene 4:1, 50 μm particle size) and subsequent recrystallisation from 100 ml of cyclohexane gives 24.0 g (45% of theory) of the title compound. $R_f=0.75$ (toluene)

EXAMPLE II 4-(Bromomethyl)-3-chlorobenzenesulphonyl chloride

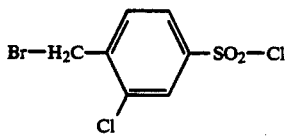

45.9 g (0.2 mol) of sodium 3-chloro-4-methylbenzenesulphonate are mixed with 83.3 g (0.4 mol) of phosphorus pentachloride and the mixture is heated at an oil bath temperature of 140° C. for 30 minutes. 500 ml of toluene are added while the mixture is hot, and the resulting solution is heated to boiling point and, after cooling, poured onto ice. The organic phase is separated off and washed with water (2×200 ml). After drying over MgSO₄, the organic phase is filtered, and all the volatile substances are stripped off in vacuo. The resulting residue is purified by flash chromatography (petroleum ether/toluene 4:1, 50μ particle size). 24.9 g of a product which is immediately reacted further are obtained:

The product is taken up in 200 ml of carbon tetrachloride and, after addition of 19.6 g (0.11 mol) of N-bromosuccinimide and 0.1 g (0.6 mmol) of ABN, the mixture is heated under reflux for 6 hours. After cooling, the solids are filtered off and the filtrate is freed from the solvent. Flash chromatography (petroleum ether/toluene 4:1, 50μ particle size) gives 21.2 g (35%) of the title compound. $R_f=0.32$ (petroleum ether/methylene chloride 4:1)

EXAMPLE III 4-(Bromomethyl)-benzenesulphonyl-N-pyrrolidinide

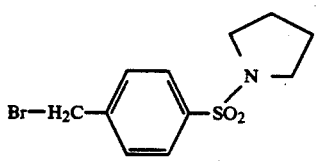

5.3 g (0.02 mol) of the compound from Example I are dissolved in 200 ml of methylene chloride and 4.0 g (0.04 mol) of triethylamine, and, after addition of 1.4 g (0.02 mol) of pyrrolidine in 50 ml of methylene chloride at 0° C., the mixture is subsequently stirred at 0° C. for 1 hour. It is extracted with 2N HCl (2×100 ml) and H₂O (2×100 ml), dried over MgSO₄ and filtered, and all the volatile contents are evaporated in vacuo. Yield: 5.4 g (89% of theory) $R_f=0.09$ (toluene)

EXAMPLE IV 4-(Bromomethyl)benzenesulphonyl-N-piperidinide

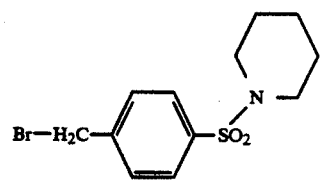

Analogously to the instructions of Example III, 1.0 g (81% of theory) of the title compound is obtained from 1.1 g (4 mmol) of the compound from Example I and 0.34 g (4 mmol) of piperidine. $R_f=0.14$ (toluene)

EXAMPLE V (S)-4-(Bromomethyl)-benzenesulphonyl-N-2-(tert-butoxycarbonyl)pyrrolidinide

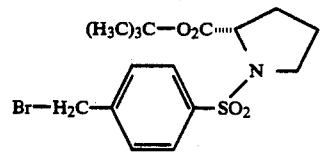

Analogously to the instructions of Example III, 9.1 g (84% of theory) of the title compound are obtained from 7.25 g (27 mmol) of the compound from Example I and 4.6 g (27 mmol) of S-proline tert-butyl ester. $R_f=0.66$ (petroleum ether/ethyl acetate 7:3)

EXAMPLE VI rac-4-(Bromomethyl)-benzenesulphonyl-N-2-(tert-butoxycarbonyl)piperidinide

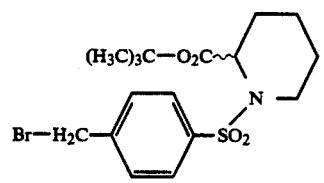

Analogously to the instructions of Example III, 7.4 g (59% of theory) of the title compound are obtained from 8.0 g (30 mmol) of the compound from Example I and 5.5 g (30 mmol) of rac-pipecolinic acid tert-butyl ester. $R_f=0.53$ (petroleum ether/ethyl acetate 5:1)

EXAMPLE VII (S)-4-(Bromomethyl)-3-chlorobenzenesulphonyl-N-2-(tert-butoxycarbonyl)pyrrolidinide

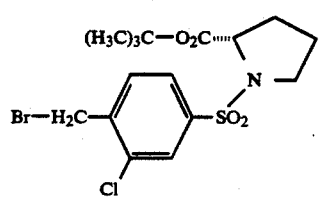

Analogously to the instructions of Example III, 13.9 g (96% of theory) of the title compound are obtained from 10.0 g (33 mmol) of the compound from Example II and 5.7 g (33 mmol) of S-proline tert-butyl ester. $R_f=0.55$ (petroleum ether/ethyl acetate 7:3)

EXAMPLE VIII rac-4-(Bromomethyl)-3-chlorobenzenesulphonyl-N-2-(tert-butoxycarbonyl)piperidinide

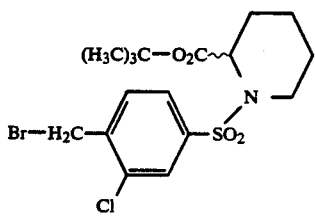

Analogously to the instructions of Example III, 14.6 g (98% of theory) of the title compound are obtained from 10.0 g (33 mmol) of the compound from Example II and 6.1 g (33 mmol) of rac-pipecolinic acid tert-butyl ester. $R_f=0.6$ (petroleum ether/ethyl acetate 7:3)

EXAMPLE IX

N-Trifluoroacetyl-L-prolinamide

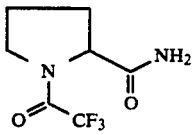

30 g (0.142 mol) of trifluoroacetylproline are initially introduced into 150 ml of dimethylformamide under an inert gas. 142.6 ml (0.1704 mol) of 38% strength PPA in ethyl acetate are added at $-20°$ C. Ammonia is passed in until the mixture is saturated, a white precipitate separating out after 30 minutes. The mixture is thawed under a weak stream of ammonia. The entire reaction mixture is then poured into 600 ml of H$_2$O and acidified to pH 4 with concentrated acetic acid. It is extracted by shaking with $4\times200$ ml of methylene chloride and with $3\times200$ ml of ether. The combined organic phases are dried with magnesium sulphate and the solvent is stripped off. The residues are chromatographed together over silica gel 60 F254, methylene chloride/methanol (10:1). The fractions containing the product are freed from the solvent on a rotary evaporator. 17.12 g of the title compound are obtained (57% of theory); $R_f=0.345$ (toluene/ethylacetate/CH$_3$COOH) 20:20:1

EXAMPLE X

2-Cyano-N-trifluoroacetyl-pyrrolidine

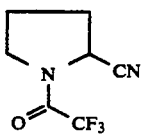

40 g (0.19 mol) of the product from Example IX and 45 g =46 ml (0.57 mol) of pyridine are initially introduced into 300 ml of tetrahydrofuran under an inert gas. 48 g =32.25 ml (0.228 mol) of trifluoroacetic anhydride are added dropwise at 0° C. The reaction mixture is subsequently stirred at 0° C. for 30 minutes and at room temperature for 90 minutes. The mixture is then poured into 1 l of 1N hydrochloric acid and extracted by shaking with $3\times200$ ml of methylene chloride. The combined organic phases are extracted by shaking with 200 ml of saturated NaCl solution and dried over magnesium sulphate. The solvent is stripped off and the residue is chromatographed over silica gel 60 F254. Petroleum ether/ethyl acetate/acetic acid (1600:200:5). The fractions containing the product are concentrated. 32.4 g of the title compound are obtained (88.8% of theory). $R_f$: 0.57 (petrolemether/ethyl acetate 7:3).

EXAMPLE XI

2-Tetrazolyl-N-trifluoroacetyl-pyrrolidine

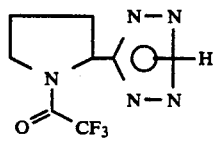

31.35 g=32.6 ml (0.26 mol) of diethylaluminium chloride are initially introduced into 65 ml of toluene under an inert gas. 29.95 g=34.04 ml (0.26 mol) of trimethylsilyl azide are added at room temperature, and the mixture is subsequently stirred at room temperature for 10 minutes. 25 g (0.13 mol) of the product from Example X, dissolved in 65 ml of toluene, are added at 0° C. The reaction mixture is stirred at 0° C. for 30 minutes, at room temperature for 120 minutes and at 40° C. for 60 minutes. Saturated potassium fluoride solution is added to the cooled mixture until no further evolution of gas is detectable.

The reaction mixture is added to 600 ml of H$_2$O, acidified to pH 4 and extracted with $3\times100$ ml of ethyl acetate. 50 ml of n-hexane are added to the combined organic phases. About ⅓ of the solvent is distilled over a distillation bridge, without cooling, in order to remove the azides. The residue is dried over magnesium sulphate and freed from the solvent on a rotary evaporator. 18.54 g of the title compound (60.6% of theory) are obtained. $R_f$: 0.4 (toluene/ethyl acetate 1:1).

EXAMPLE XII

N-Trifluoroacetyl-2-[N-trityl-tetrazolyl]pyrrolidine

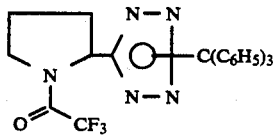

16.23 g (0.069 mol) of the product from Example XI and 10.47 g=14.35 ml (0.1035 mol) of triethylamine are initially introduced into 70 ml of methylene chloride. 19.83 g (0.069 mol) of triphenylmethyl chloride are then added. The reaction mixture is subsequently stirred at room temperature for 1.5 hours, diluted with methylene chloride and extracted with buffer solution of pH=5 ($3\times50$ ml). The organic phase is dried over magnesium sulphate. The solvent is stripped off on a rotary evaporator. The residue is stirred with ether. The resulting crystals are filtered off with suction and dried. 24.65 g of the title compound (75% of theory) are obtained. R$_f$: 0.53 (petroleum ether/ethyl acetate 7:3).

EXAMPLE XIII 2-(N-Trityl-tetrazolyl)pyrrolidine

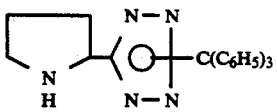

24 g (0.05 mol) of the product from Example XII are initially introduced into 100 ml of ethanol under an inert gas. 2.84 g (0.075 mol) of sodium borohydride are added in portions at 0° C. The mixture is thawed, and stirred at room temperature for 1 hour. 6 μl of acetic acid are added and the entire reaction mixture is poured into 500 ml of buffer solution of pH 9. The mixture is extracted with 3×75 ml of methylene chloride. The combined organic phases are dried over magnesium sulphate and freed from the solvent on a rotary evaporator. The residue is chromatographed over silica gel 60 F254. Petroleum ether/ethyl acetate (7:3). The corresponding fractions are concentrated and the residue is dried. 7.16 g of the title compound (37.5% of theory) are obtained. R$_f$: 0.22 (ethyl acetate).

EXAMPLE XIV

4-Bromomethyl-3-chloro-benzenesulphonic acid 2-[trityltetrazolyl]pyrrolidinide

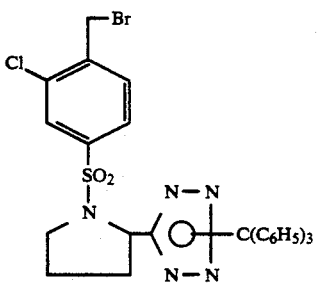

Analogously to the instructions of Example III, 6.49 g of the title compound (95% of theory) are obtained from 3.19 g (10.5 mmol) of the compound from Example II and 4 g (10.5 mmol) of the compound from Example XIII. R$_f$: 0.53 (petroleum ether/ethyl acetate 7:3).

EXAMPLE XV 4-(Bromomethyl)-3-fluorobenzenesulphonyl chloride

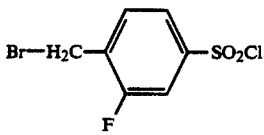

20.9 g (0.1 mol) of 3-fluoro-4-methylbenzenesulphonyl chloride are taken up in 200 ml of carbon tetrachloride and, after addition of 19.6 g (0.11 mol) of N-bromosuccinimide and 0.3 g of dibenzoyl peroxide, the mixture is heated under reflux for 5 hours. After cooling, the solids are filtered off and the filtrate is freed from the solvent. Flash chromatography with petroleum ether/toluene (4:1), 50 μm particle size, gives 12.4 g (44% of theory) of the title compound. R$_f$: 0.42 (petroleum ether/toluene 3:1).

EXAMPLE XVI 4-(Bromomethyl)-3-trifluoromethylbenzenesulphonyl chloride

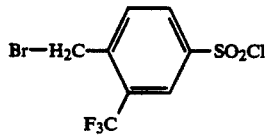

64.6 g (0.25 mol) of 3-trifluoromethyl-4-methylbenzenesulphonyl chloride are taken up in 500 ml of carbon tetrachloride and, after addition of 44.5 g (0.25 mol) of N-bromosuccinimide and 0.4 g of ABN, the mixture is heated under reflux for 24 hours. After cooling, the solids are filtered off and the filtrate is freed from the solvent. Flash chromatography with petroleum ether/toluene (4:1), 50 μm particle size, gives 33.9 g (40% of theory) of the title compound. R$_f$: 0.41 (petroleum ether/toluene 3:1).

EXAMPLE XVII (S)-4-(Bromomethyl)-3-fluorobenzenesulphonyl-N-2-(tert-butoxy-carbonyl)pyrrolidinide

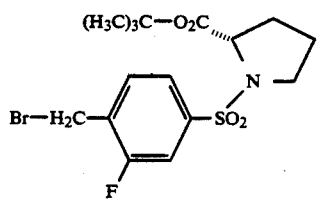

Analogously to the instructions from Example III, 12.7 g (100% of theory) of the title compound are obtained from 8.6 g (30 mmol) of the compound from Example XV and 5.1 g (30 mmol) of S-proline tert-butyl ester. R$_f$: 0.57 (petroleum ether/ethyl acetate 7:3).

EXAMPLE XVIII (S)-4-(Bromomethyl)-3-trifluoromethylbenzenesulphonyl-N-2-(tert-butoxycarbonyl)pyrrolidinide

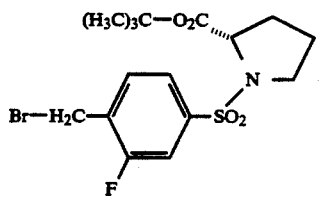

Analogously to the instructions of Example III, 23.6 g (100% of theory) of the title compound are obtained from 16.9 g (50 mmol) of the compound from Example XVI and 8.6 g (50 mmol) of S-proline tert-butyl ester. R$_f$: 0.63 (petroleum ether/ethyl acetate 7:3).

EXAMPLE XIX (S)-4-carboxy-3-hydroxybenzenesulphonyl-N-2-(tert.-butoxycarbonyl)-pyrrolidinide

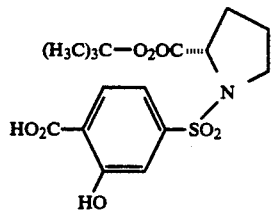

Analogously to the method of Example III, 30.0 g (81% of theory) of the title compound are obtained from 23.7 g of 4-carboxy-3-hydroxybenzenesulphochloride (100 mmol) and 17.1 g (100 mmol) of S-proline tert.-butyl ester. $R_f$: 0.18 (acetone)

EXAMPLE XX (S)-4-Benzyloxycarbonyl-3-benzyloxybenzenesulphonic acid N-2-(tert.-butoxycarbonyl)-pyrrolidinide

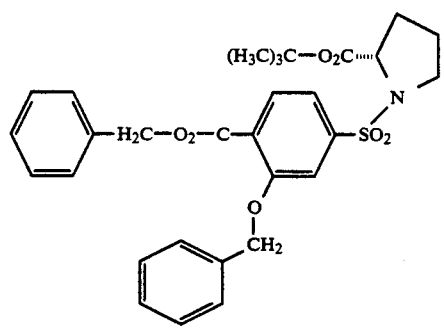

28.3 g of $K_2CO_3$ (204 mmol) and 25.7 g (150 mmol) of benzyl bromide are added to 25.3 g (68 mmol) of the compound of Example XIX dissolved in 200 ml of DMF. The reaction mixture is stirred for a further 2 hours at 75° C. and cooled. 1 l of water is then added and the mixture is extracted with ethyl acetate (3×400 ml) and the extract washed with water (5×400 ml), dried over $MgSO_4$, filtered and all the volatile components are stripped off in vacuo. The product is purified by flash chromatography (petroleum ether/$CH_2Cl_2$ 5:1 and petroleum ether/ethyl acetate 6:1, particle size: 50μ) and then purified further by recrystallization from 600 ml of a solvent mixture (petroleum ether/ethyl acetate 6:1). 35.5 g (95% of theory) of the title compound are obtained. $R_f$=0.53 (petroleum ether/ethyl acetate 7:3)

EXAMPLE XXI (S)-4-(Hydroxymethyl)-3-benzyloxybenzenesulphonic acid N-2-(tert.-butoxycarbonyl)-pyrrolidinide

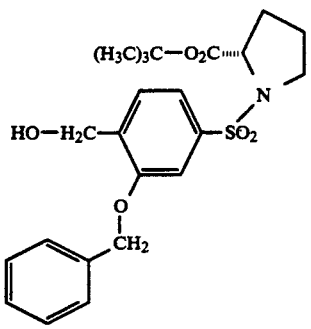

11.03 g (20 mmol) of the compound of Example XX are dissolved in 100 ml of diglyme and, after adding 1.51 g (40 mmol) of sodium borohydride and 1.68 g (40 mmol) of LiCl, the mixture is stirred for 4 hours at 70° C. After cooling, 500 ml of water are added to the reaction mixture, which is then acidified with 1N HCl to a pH of 3. The mixture is extracted with ether (3×300 ml) and the extract is washed with water (6×300 ml), dried over $MgSO_4$ and the filtrate freed from the solvent. The residue is chromatographed on silica gel 60 F 254 (petroleum ether/ethyl acetate (7:3)). The corresponding fractions are concentrated by evaporation and dried. 5.0 g (56% of theory) of the title compound are obtained. $R_f$=0.36 (petroleum ether/ethyl acetate 7:3)

EXAMPLE XXII (S)-4-(Bromomethyl)-3-benzyloxybenzenesulphonic acid N-2-(tert.butoxycarbonyl)-pyrrolidinide

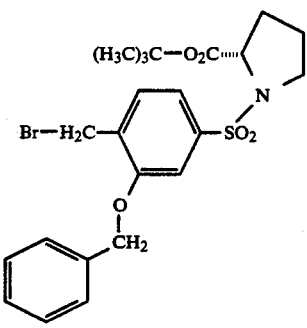

2.24 g (5 mmol) of the compound from Example XXI are initially introduced into 20 ml of absolute DMF under an inert gas. 2.53 g (6 mmol) of triphenylphosphine dibromide are added at 0° C. The reaction mixture is stirred for 1 hour at room temperature. 200 ml of water are added, the mixture is extracted with ethyl acetate (3×80 ml) and the extract is washed with water (5×60 ml), dried over $MgSO_4$, filtered and all the volatile components are stripped off in vacuo. The product is purified by flash chromatography ($CH_2Cl_2$, particle size: 50μ) and 2.55 g (100% of theory) of the title compound are obtained.

$R_f$=0.56 (petroleum ether/ethyl acetate 7:3)

PREPARATION EXAMPLES

EXAMPLE 1

4-[(2-Butyl-4-chloro-5-formylimidazolyl)methyl]benzenesulphonyl-N-pyrrolidinide

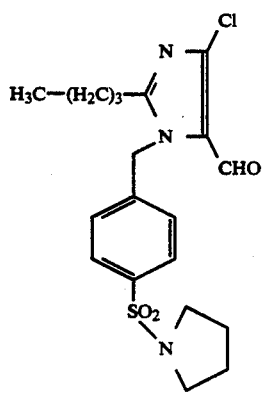

180 mg (6.0 mmol) of an 80% strength dispersion of sodium hydride in mineral oil are added to 1.1 g (6.0 mmol) of 2-butyl-4-chloro-5-formylimidazole in 12 ml of dimethylformamide, and the mixture is stirred at 20° C. for 30 minutes. It is cooled to 0° C. and 1.8 g (6.0 mmol) of the compound from Example III in 15 ml of dimethylformamide are added. The reaction mixture is subsequently stirred at 20° C. for 2.5 hours, poured onto ice and extracted with ethyl acetate (3×50 ml), the combined organic phases are washed with saturated sodium chloride solution (5×50 ml), dried over MgSO4 and filtered, and all the volatile constituents are stripped off in vacuo. The crude product is purified by flash chromatography (petroleum ether/ethyl acetate 10:1→3:1, 50μ particle size) to give 1.1 g (60% of theory) of the title compound. $R_f$=0.14 (toluene).

EXAMPLE 2

4-[(2-Butyl-4-chloro-5-formylimidazolyl)methyl]benzenesulphonyl-N-piperidinide

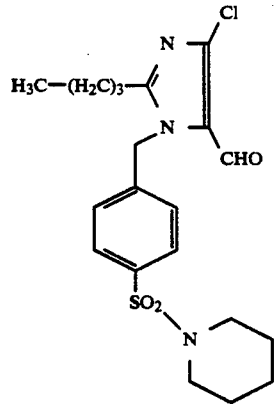

Analogously to the instructions of Example 1, 3.1 g (61% of theory) of the title compound are obtained from 3.8 g (12.0 mmol) of the compound from Example III and 2.2 g of 2-butyl-4-chloro-5-formylimidazole. $R_f$=0.39 (petroleum ether/ethyl acetate 7:3)

EXAMPLE 3

(S)-4-[(2-Butyl-4-chloro-5-formylimidazolyl)methyl]benzenesulphonyl-N-(2-tert-butoxycarbonyl)pyrrolidinide

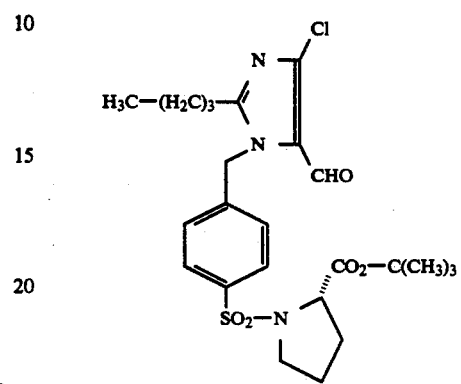

Analogously to the instructions of Example 1, 6.0 g (74% of theory) of the title compound are obtained from 9.1 g (23 mmol) of the compound of Example V and 3.0 g (16 mmol) of 2-butyl-4-chloro-5-formylimidazole. $R_f$=0.61 (petroleum ether/ethyl acetate 7:3)

EXAMPLE 4 rac-4-[(2-Butyl-4-chloro-5-formylimidazolyl)methyl]benzenesulphonyl-N-(2-tert-butoxycarbonyl)piperidinide

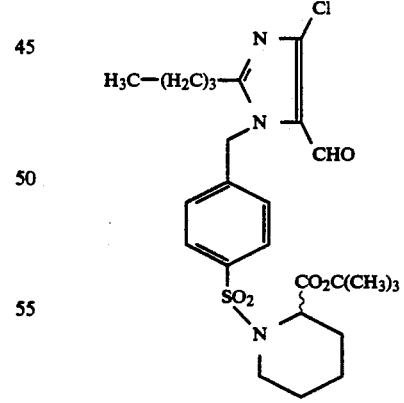

Analogously to the instructions of Example 1, 4.9 g (53% of theory) of the title compound are obtained from 7.4 g (18 mmol) of the compound from Example VI and 3.3 g (18 mmol) of 2-butyl-4-chloro-5-formylimidazole. $R_f$=0.08 (petroleum ether/ethyl acetate 7:1)

EXAMPLE 5

(S)-4-[(2-Butyl-4-chloro-5-formylimidazolyl)methyl]-3-chlorobenzenesulphonyl-N-(2-tert-butoxycarbonyl)-pyrrolidinide

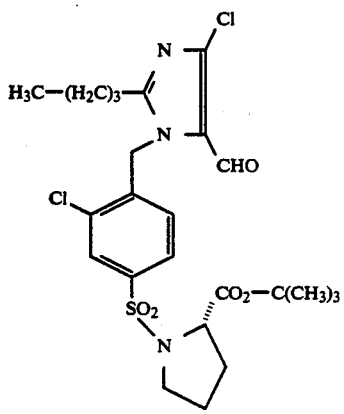

Analogously to the instructions of Example 1, 2.7 g (42% of theory) of the title compound are obtained from 6.6 g (15 mmol) of the compound from Example VII and 2.2 g (12 mmol) of 2-butyl-4-chloro-5-formylimidazole. $R_f=0.75$ (dichloromethane/ethyl acetate 10:1)

EXAMPLE 6 rac-4-[(2-Butyl-4-chloro-5-formylimidazolyl)methyl]-3-chlorobenzenesulphonyl-N-(2-tert-butoxycarbonyl)-piperidinide

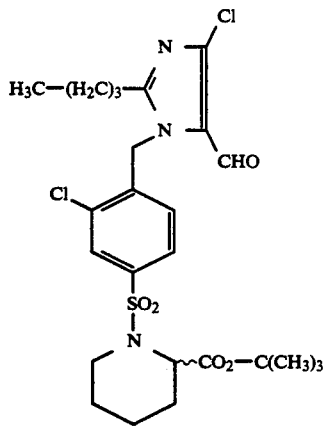

Analogously to the instructions of Example 1, 2.4 g (26% of theory) of the title compound are obtained from 6.8 g (15 mmol) of the compound from Example VIII and 2.2 g (12 mmol) of 2-butyl-4-chloro-5-formylimidazole. $R_f=0.87$ (dichloromethane/ethyl acetate 10:1)

EXAMPLE 7 rac-4-[5-Carboxy-4-chloro-2-butylimidazolyl)methyl]-benzenesulphonyl-N-(2-tert-butoxycarbonyl)piperidinide

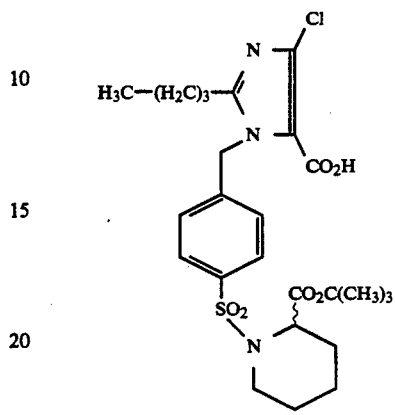

255 mg (0.5 mmol) of the compound from Example 3 are dissolved in 3 ml of tert-butanol, 2 ml of a 1.25M $NaH_2PO_4$ solution (brought to pH=7 with NaOH) are added, and addition of 3 ml of a 1M $KMnO_4$ solution follows. The mixture is subsequently stirred at 20° C. for 10 minutes, and 5 ml of a saturated $Na_2SO_4$ solution are added. The pH is brought to 4 with concentrated HCl and the mixture is extracted with ethyl acetate (3 portions of 50 ml). The combined organic phases are washed with $H_2O$ (3×50 ml), dried over $MgSO_4$ and freed from the solvent. 258 mg (98% of theory) of the above title compound are obtained. $R_f=0.14$ (dichloromethane/MeOH 10:1)

EXAMPLE 8 rac-4-[5-carboxy-4-chloro-2-butylimidazolyl]methyl-benzenesulphonyl-N-(2-carboxy)piperidide

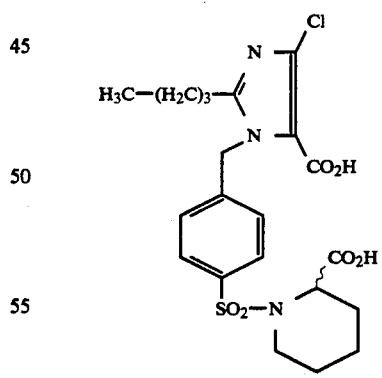

158 mg (0.3 mmol) of the compound from Example 7 are dissolved in 10 ml of methylene chloride, and 2 ml of trifluoroacetic acid are added. The mixture is subsequently stirred at 20° C. for 4 hours, 50 ml of methylene chloride are added, the mixture is washed with ice-water (3×50 ml), dried over $MgSO_4$ and filtered, and all the volatile constituents are stripped off in vacuo to give 101 mg (72% of theory) of the title compound. $R_f=0.10$ ($CH_2Cl_2$/MeOH 3:1)

EXAMPLE 9 instructions of Examples 1-9, the compounds listed in Table 1 are prepared:

TABLE 1

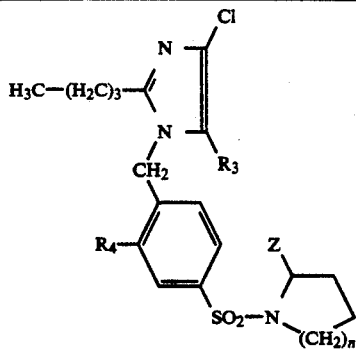

| Ex. No. | R³ | R⁴ | n | Z | Configuration | Yield** (% of theory) | $R_f$* solvent |
|---|---|---|---|---|---|---|---|
| 10 | —CH₂OH | H | 1 | H | — | 79.4 | 0.18$^a$ |
| 11 | —CH₂OH | H | 2 | H | — | 82.2 | 0.14$^a$ |
| 12 | —CH₂OH | Cl | 1 | —CO₂C(CH₃)₃ | S | 96.3 | 0.28$^b$ |
| 13 | —CH₂OH | Cl | 2 | —CO₂C(CH₃)₃ | rac | 95.5 | 0.32$^b$ |
| 14 | —CH₂OH | H | 1 | —CO₂C(CH₃)₃ | S | 88.3 | 0.16$^b$ |
| 15 | —CO₂H | H | 1 | —CO₂H | S | 70.2 (2 stages) | 0.06$^c$ |
| 16 | —CO₂H | Cl | 2 | —CO₂H | rac | 76.8 (2 stages) | 0.19$^c$ |
| 17 | —CO₂H | H | 1 | —CO₂C(CH₃)₃ | S | 98.0 | 0.13$^d$ |
| 18 | —CO₂H | Cl | 2 | —CO₂C(CH₃)₃ | rac | 86.3 | 0.22$^d$ |
| 19 | —CH₂OH | Cl | 1 | —CO₂H | S | 97.9 | 0.11$^d$ |
| 20 | —CH₂OH | Cl | 2 | —CO₂H | rac | 91.5 | 0.21$^d$ |
| 21 | —CH₂OH | H | 1 | —CO₂H | S | 87.6 | 0.09$^d$ |
| 22 | —CO₂H | Cl | 1 | —CO₂C(CH₃)₃ | S | 77.0 | 0.17$^d$ |
| 23 | —CO₂H | H | 2 | —CO₂C(CH₃)₃ | rac | 85.4 | 0.19$^d$ |
| 24 | —CO₂H | Cl | 1 | —CO₂H | S | 86.1 | 0.17$^c$ |
| 25 | —CO₂H | H | 2 | —CO₂H | rac | 97.4 | 0.26$^c$ |

**starting from the aldehyde (including hydrolysis)

rac-4-[2-Butyl-4-chloro-5-(hydroxymethyl)imidazolyl]-methyl-3-chlorobenzenesulphonyl-N-(2-tert-butoxycarbonyl)piperidide

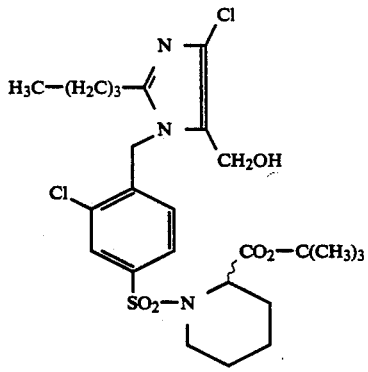

223 mg (0.4 mmol) of the compound from Example 6 are dissolved in 5 ml of tetrahydrofuran, and 30 mg (0.8 mmol) of NaBH₄ in 2 ml of 0.01N NaOH are added. The mixture is subsequently stirred at 20° C. for 30 minutes and 1N HCl is then added dropwise, while cooling with ice, until the evolution of gas has ended. The organic phase is separated off and the aqueous phase is extracted with ethyl acetate (2×50 ml). The combined organic phases are washed with H₂O (3×50 ml), dried over MgSO₄, filtered and freed from the solvent. 214 mg (96% of theory) of the title compound are obtained. $R_f$=0.35 (CH₂Cl₂/ethyl acetate 5:1) Analogously to the

EXAMPLE 26

(S)-4-[(2-Butyl-5-formylimidazolyl)methyl]-3-chlorobenzenesulphonyl-N-(2-tert-butoxycarbonyl)-pyrrolidinide

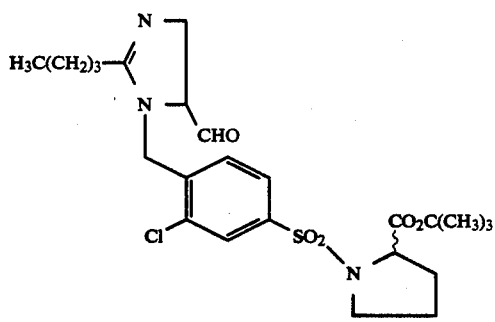

4.98 g (9.15 mmol) of the compound from Example 5 are dissolved in 100 ml of tetrahydrofuran/50 ml of methanol and hydrogenated in the presence of 1.24 g (9.15 mmol) of sodium acetate trihydrate and 0.5 g of palladium-on-active-charcoal (5%) under a hydrogen pressure of about 3 bar for 1 hour. The catalyst is then filtered off, the mixture is concentrated and the residue is purified over silica gel with ethyl acetate/petroleum ether (1:1 and 2:1). Yield: 3.3 g (71% of theory). $R_f$=0.18 (ethyl acetate/petroleum ether=1:1).

We claim:

1. A sulphonylbenzyl-substituted imidazole of the formula:

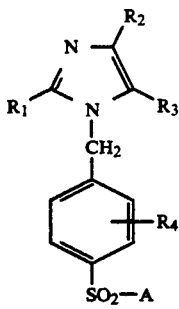

in which
- $R_1$ represents straight-chain or branched alkyl or alkenyl having in each case up to 8 carbon atoms, which are optionally substituted by cycloalkyl having 3 to 6 carbon atoms, or represents cycloalkyl having 3 to 8 carbon atoms;
- $R_2$ represents hydrogen or halogen, or represents straight-chain or branched perfluoroalkyl having up to 8 carbon atoms;
- $R_3$ represents straight-chain or branched alkyl having up to 6 carbon atoms, which is substituted by hydroxyl or straight-chain or branched alkoxy having up to 4 carbon atoms, or represents a group of the formula $-CO-R_5$ or $-CO-NR_6R_7$;

wherein
- $R_5$ represents hydrogen, straight-chain or branched alkoxy having up to 8 carbon atoms, hydroxyl, benzyloxy or phenoxy;
- $R_6$ and $R_7$ are identical or different and represent hydrogen, straight-chain or branched alkyl having up to 8 carbon atoms or phenyl;
- $R_4$ represents hydrogen, halogen or straight-chain or branched alkyl having up to 8 carbon atoms; or represents straight-chain or branched perfluoroalkyl having up to 6 carbon atoms; or represents a group of the formula $-OX$;

wherein
- X represents hydrogen, benzyl, acetyl, or represents straight-chain or branched alkyl having up to 8 carbon atoms;
- A represents a heterocyclic ring radical which is bound via a ring nitrogen atom, said heterocyclic ring radical being selected from the group consisting of azetidinyl, piperidinyl, piperazinyl or morpholinyl, each of which is optionally substituted by one or two substituents independently selected from the group consisting of perfluoroalkyl having up to 5 carbon atoms, $-SO_3H$, $-CO-R^9$, $-CONR^{10}R^{11}$,

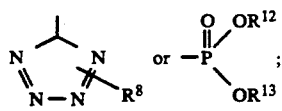

wherein
- $R^8$ represents hydrogen, straight-chain or branched alkyl having up to 6 carbon atoms or triphenylmethyl;
- $R^9$ represents hydrogen, straight-chain or branched alkoxy having up to 8 carbon atoms, hydroxyl, benzyloxy or phenoxy;
- $R^{10}$ and $R^{11}$ independently represent hydrogen, straight-chain or branched alkyl having up to 8 carbon atoms or phenyl; and
- $R^{12}$ and $R^{13}$ are identical or different and represent hydrogen, straight-chain or branched alkyl having up to 8 carbon atoms or phenyl;

or a salt thereof.

2. A sulphonylbenzyl-substituted imidazole according to claim 1, wherein
- $R_1$ represents straight-chain or branched alkyl or alkenyl having in each case up to 6 carbon atoms, which are optionally substituted by cyclopropyl, cyclobutyl, cyclopentyl or cyclohexyl; or represents cyclopropyl, cyclobutyl, cyclopentyl or cyclohexyl;
- $R_2$ represents hydrogen or fluorine, chlorine or bromine, or represents straight-chain or branched perfluoroalkyl having up to 6 carbon atoms;
- $R_3$ represents straight-chain or branched alkyl having up to 4 carbon atoms, which is substituted by hydroxyl, methoxy or ethoxy, or represents a group of the formula $-CO-R_5$ or $-CO-NR_6R_7$;

wherein
- $R_5$ represents hydrogen, straight-chain or branched alkoxy having up to 6 carbon atoms, hydroxyl, benzyloxy or phenoxy;
- $R_6$ and $R_7$ are identical or different and represent hydrogen or straight-chain or branched alkyl having up to 6 carbon atoms;
- $R_4$ represents hydrogen, fluorine, chlorine or bromine or straight-chain or branched alkyl having up to 6 carbon atoms; or represents straight-chain or branched perfluoroalkyl having up to 4 carbon atoms; or represents a group of the formula $-OX$;

wherein
- X represents hydrogen, benzyl, acetyl, or represents straight-chain or branched alkyl having up to 6 carbon atoms;
- A represents a heterocyclic ring radical which is bound via a ring nitrogen atom, said heterocyclic ring radical being selected from the group consisting of azetidinyl, piperidinyl, piperazinyl or morpholinyl, each of which is optionally substituted by one or two substituents independently selected from the group consisting of trifluoromethyl, $-SO_3H$, $-CO-R^9$, $-CONR^{10}R^{11}$,

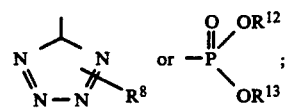

wherein
- $R^8$ represents hydrogen, straight-chain or branched alkyl having up to 4 carbon atoms or triphenylmethyl;
- $R^9$ represents hydrogen, straight-chain or branched alkoxy having up to 6 carbon atoms, hydroxyl, benzyloxy or phenoxy;
- $R^{10}$ and $R^{11}$ independently represent hydrogen or straight-chain or branched alkyl having up to 6 carbon atoms; and
- $R^{12}$ and $R^{13}$ are identical or different and represent hydrogen, straight-chain or branched alkyl having up to 6 carbon atoms or phenyl; or a salt thereof.

3. A sulphonylbenzyl-substituted imidazole according to claim 1, wherein $R_1$ represents straight-chain or branched alkyl or alkenyl having in each case up to 4 carbon atoms or cyclopropyl;

$R_2$ represents hydrogen, fluorine or chlorine, or represents straight-chain or branched perfluoroalkyl having up to 4 carbon atoms;

$R_3$ represents —CH$_2$OH, or represents a group of the formula —CO—$R_5$ or —CO—NR$_6$R$_7$;

wherein $R_5$ represents hydrogen, straight-chain or branched alkoxy having up to 4 carbon atoms, hydroxyl, benzyloxy or phenoxy;

$R_6$ and $R_7$ are identical or different and represent hydrogen or straight-chain or branched alkyl having up to 4 carbon atoms;

$R_4$ represents hydrogen, fluorine, chlorine or straight-chain or branched alkyl having up to 4 carbon atoms; or represents straight-chain or branched perfluoroalkyl having up to 3 carbon atoms; or represents a group of the formula —OX;

wherein

X represents hydrogen, benzyl, acetyl, or represents straight-chain or branched alkyl having up to 6 carbon atoms;

A represents piperidinyl, which is optionally substituted by one or two substituents independently selected from the group consisting of trifluoromethyl, —SO$_3$H, —CO—R$^9$, —CONR$^{10}$R$^{11}$,

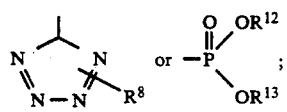

wherein $R^8$ represents hydrogen, methyl, ethyl or triphenylmethyl;

$R^9$ represents hydrogen, straight-chain or branched alkoxy having up to 4 carbon atoms, hydroxyl, benzyloxy or phenoxy;

$R^{10}$ and $R^{11}$ independently represent hydrogen or straight-chain or branched alkyl having up to 4 carbon atoms; and $R^{12}$ and $R^{13}$ are identical or different and represent hydrogen, straight-chain or branched alkyl having up to 4 carbon atoms or phenyl;

or a salt thereof.

4. A compound according to claim 1, wherein such compound is 4-[(2-butyl-4-chloro-5-carboxy-imidazolyl)methyl]benzene-sulphonyl-N-(2-carboxy)-pyrrolidimide of the formula

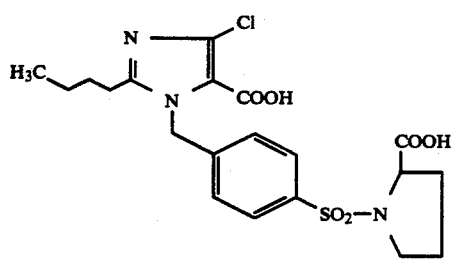

or a salt thereof.

5. A compound according to claim 1, wherein such compound is 4-[(2-butyl-4-chloro-5-carboxy-imidazolyl)methyl]-(3-chloro-benzene)-sulphonyl-N-(2-carboxy)piperidimide of the formula

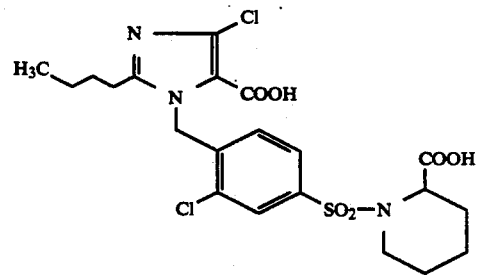

or a salt thereof.

6. A compound according to claim 1, wherein such compound is 4-[(2-butyl-4-chloro-5-hydroxy-methyl-imidazolyl)methyl]-(3-chloro-benzene)-sulphonyl-N-(2-carboxy)pyrrolidimide of the formula

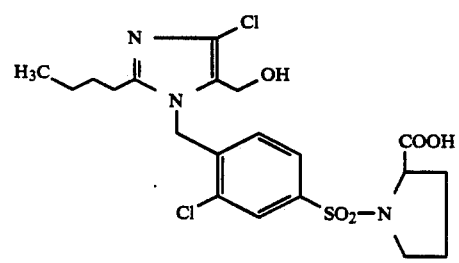

or a salt thereof.

7. A compound according to claim 1, wherein such compound is 4-[(2-butyl-4-chloro-5-hydroxy-methyl-imidazolyl)methyl]benzene-sulphonyl-N-(2-carboxy)-pyrrolidimide of the formula

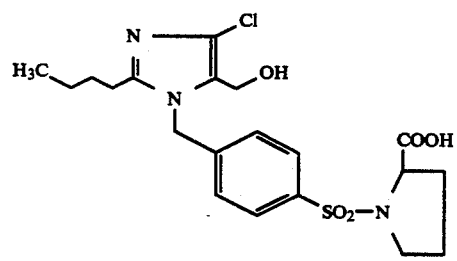

or a salt thereof.

8. A compound according to claim 1, wherein such compound is 4-[(2-butyl-4-chloro-5-carboxy-imidazolyl)methyl]benzene-sulphonyl-N-(2-carboxy)-piperidimide of the formula

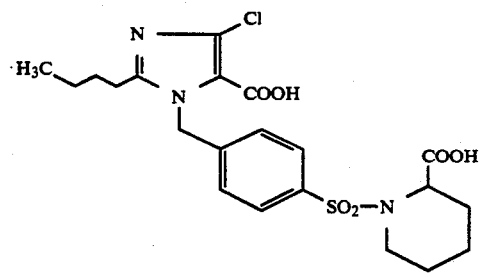

or a salt thereof.

9. A composition for the treatment of atriable hypertension and arteriosclerosis comprising an amount effective therefor of a compound or salt thereof according to claim 1 and a pharmacologically acceptable diluent.

10. The method of treating atriable hypertension and arteriosclerosis in a patient in need thereof which comprises administering to such patient an amount effective therefor of a compound and salt thereof according to claim 1.

* * * * *